United States Patent
Kosugi (10) Patent No.: US 6,334,708 B1
(45) Date of Patent: Jan. 1, 2002

(54) MEDICAL IMAGE RADIOGRAPHY APPARATUS

(75) Inventor: Norimitsu Kosugi, Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/476,126

(22) Filed: Jan. 3, 2000

(30) Foreign Application Priority Data

Jan. 6, 1999 (JP) ............................................ 11-001137

(51) Int. Cl.⁷ .............................. H05G 1/02; A61B 6/14
(52) U.S. Cl. ........................ 378/197; 378/20; 378/68; 378/205
(58) Field of Search ................................ 378/195, 196, 378/197, 205, 208, 177, 4, 20, 62, 68, 38, 39, 40

(56) References Cited

U.S. PATENT DOCUMENTS

| 4,649,555 | A | * | 3/1987 | Matsubayashi | 378/205 |
| 5,014,292 | A | * | 5/1991 | Siczek et al. | 378/195 |
| 5,093,852 | A | * | 3/1992 | Nishikawa et al. | 378/177 |
| 5,103,469 | A | * | 4/1992 | Tanaka | 378/205 |
| 5,267,293 | A | * | 11/1993 | Virta | 378/40 |
| 5,627,868 | A | * | 5/1997 | Nobuta et al. | 378/20 |
| 5,636,259 | A | * | 6/1997 | Khutoryansky et al. | 378/197 |

* cited by examiner

*Primary Examiner*—Drew Dunn
(74) *Attorney, Agent, or Firm*—Oblon, Spivak, McClelland, Maier & Neustadt (57) ABSTRACT

A medical image radiography apparatus includes a radiography system for taking a medical image of a subject, a supporting mechanism for supporting the radiography system in various radiography positions, a memory unit for storing a plurality of radiography positions, together with their order relation, as sequential automatic positioning data, and a controller for controlling the supporting mechanism on the basis of the sequential automatic positioning data in order to change a radiography position sequentially. In this manner, the plurality of radiography positions are stored, together with their order relation, as the sequential automatic positioning data. When taking a radiograph, the radiography position is sequentially changed in accordance with the sequential automatic positioning data. As a result, the operability concerning a change in the radiography position is improved more than in the conventional case wherein a preset button is repeatedly selected.

17 Claims, 6 Drawing Sheets

MEDICAL IMAGE RADIOGRAPHY APPARATUS

BACKGROUND OF THE INVENTION

The present invention relates to a medical image radiography apparatus such as a circulatory system X-ray diagnostic apparatus and, more particularly, to an improvement in setting of a radiography position.

In angioplasty and the like, it is very important to provide a wide operation space for the operator and enable radiography of a blood vessel profile in an appropriate direction. For this purpose, in many circulatory system X-ray diagnostic apparatuses, a C-shaped arm for mounting a radiography system (an X-ray tube, an image intensifier, a TV camera, and the like) suspends from the ceiling. The C-shaped arm can perform many motions, i.e., vertical motion, main rotation motion, sliding rotation motion, and swing (isocentric rotation). The image intensifier (I. I.) can slide in the near/away direction. The bed top of a bed can move in the longitudinal and lateral directions.

Although these many movement elements provide a wide operation space for the operator and enable radiography of a blood vessel profile in an appropriate direction, they increase an operation load for the operator, and degrade the operability and reproducibility of the radiography position. The reproducibility of the radiography position is important when comparing a present radiography image with a past radiography image and subtracting a radiography image from a master image.

In order to reduce the operation load and improve the operability and the reproduciblity, a convenient function called automatic positioning is provided to most apparatuses. According to the automatic positioning function, the positions of the movement elements described above are preset as automatic positioning data to correspond to preset buttons. When a preset button corresponding to desired automatic positioning data is pressed, the positions of the movement elements are reproduced in accordance with the data.

Recently, as the radiography methods vary, the number of preset buttons tends to increase. Therefore, the correspondence between the automatic positioning data and the preset buttons becomes difficult to recognize. The operator must select a desired preset button from many buttons, leading to a cumbersome operation. This problem becomes more conspicuous particularly when radiography is repeated while successively changing the radiography position, as in an inspection for the circulatory system.

BRIEF SUMMARY OF THE INVENTION

It is an object of the present invention to provide a medical image radiography apparatus in which the radiography position can be changed successively and easily.

In order to achieve the above object, according to the present invention, there is provided a medical image radiography apparatus comprising a radiography system for taking a medical image of a subject; a supporting mechanism for supporting the radiography system in various radiography positions; a memory unit for storing a plurality of radiography positions, together with an order relation thereof, as sequential automatic positioning data; and a controller for controlling the supporting mechanism on the basis of the sequential automatic positioning data in order to change a radiography position sequentially. In this manner, the plurality of radiography positions are stored, together with their order relation, as the sequential automatic positioning data. When taking a radiograph, the radiography position is sequentially changed in accordance with the sequential automatic positioning data. As a result, the operability concerning a change in the radiography position is improved more than in the conventional case wherein a preset button is repeatedly selected.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

A preferred embodiment of the present invention will be described with reference to the accompanying drawing. The present invention can be applied to a medical image radiography apparatus, such as an X-ray diagnostic apparatus, an ultrasonic diagnostic apparatus, an X-ray computerized tomography apparatus, a nuclear medical diagnostic apparatus (a gamma camera, an SPECT, and a PET), and a magnetic resonance imaging apparatus (MRI), in which the radiography position can be changed. For the sake of descriptive convenience, an X-ray diagnostic apparatus, particularly a circulatory system X-ray diagnostic apparatus which has many movable portions and often repeats radiography while successively changing the radiography position will be described as an example.

Figure 1:
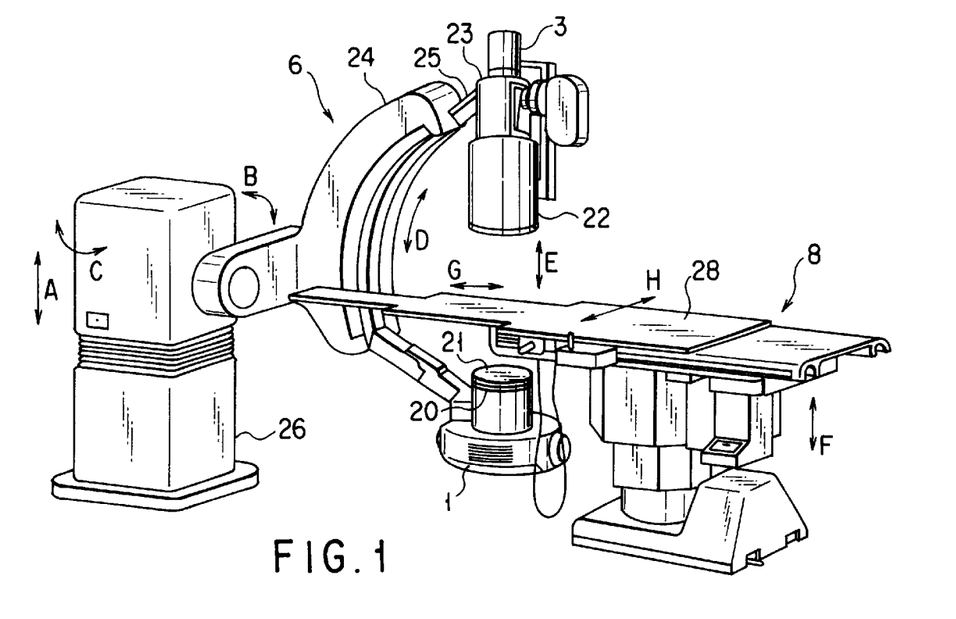
FIG. 1 is a perspective view of the gantry of a circulatory system X-ray diagnostic apparatus according to an embodiment of the present invention.

FIG. 1 is a perspective view showing the gantry of the circulatory system X-ray diagnostic apparatus according to this embodiment. An X-ray tube 1, image intensifier 22, TV camera 3, and optical system 23 constitute a radiography system. The X-ray tube 1 generates X-rays. The image intensifier 22 converts an X-ray image transmitted through a subject into an optical image. The TV camera 3 takes an optical image. The optical system 23 guides the optical image from the image intensifier 22 to the TV camera 3. A variable-aperture collimator 20 and variable-position filter 21 are arranged in front of the X-ray tube 1. An image signal output from this radiography system is converted into a digital signal by a digital fluorography (DF) unit, and is subjected to an image process such as subtraction. The obtained image is displayed and stored in a large capacity storage medium such as a magneto-optical (MO) disk.

The radiography system is supported by a supporting mechanism 6 including an arcuate arm (a C-shaped arm in this case) 25. The X-ray tube 1 is mounted on one end of the C-shaped arm 25. The image intensifier 22 is mounted on the other end of the C-shaped arm 25 to be slidable in a near/away direction E.

An arm holder 24 holds the C-shaped arm 25 to be obliquely movable (sliding rotation) in a direction D. A floor base 26 holds the arm holder 24 to be tiltable in a direction B, swingable in a direction C, and vertically movable in a direction A. In place of such a floor-installed mechanism, a suspension mechanism for suspending the arm holder 24 from the ceiling may be used. A bed top 28 for placing a subject on it is mounted on a bed 8. The bed top 28 can move in a longitudinal direction G, a lateral direction H, and a vertical direction F.

The vertical motion (direction A) of the arm holder 24, the main rotation (direction B) of the arm holder 24, the swing (direction C) of the arm holder 24, the sliding rotation motion (direction D) of the C-shaped arm 25, the sliding motion (direction E) of the image intensifier 22, the vertical motion (direction F) of the bed top 28, the longitudinal motion (direction G) of the bed top 28, and the lateral motion (direction H) of the bed top 28 determine the radiography position of the radiography system with respect to the subject.

Figure 2:
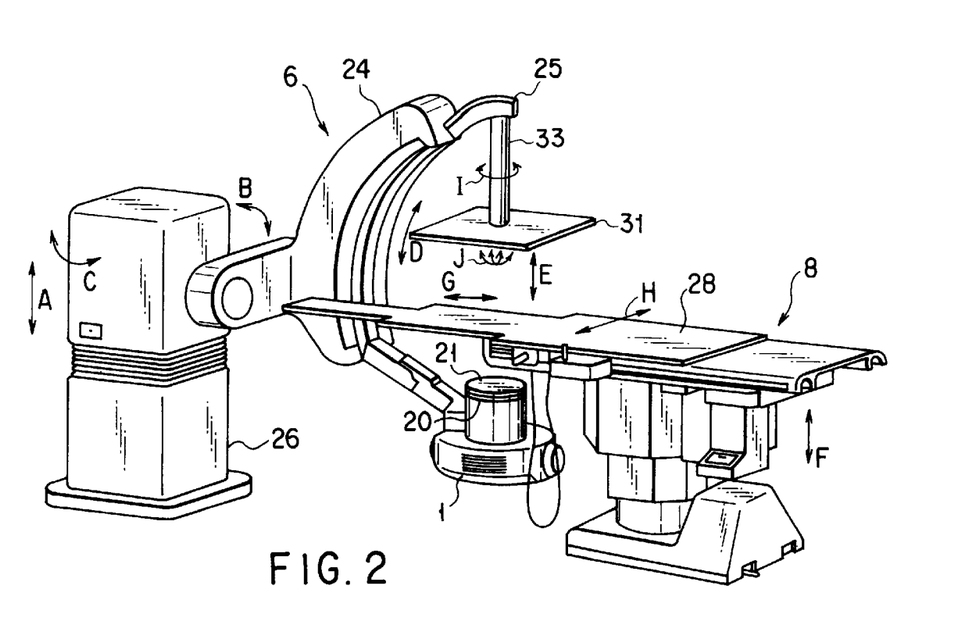
FIG. 2 is a perspective view of another gantry of FIG. 1.

As shown in FIG. 2, the radiography system may be comprised of an X-ray tube 1 and planar type X-ray detector 31. The planar type X-ray detector 31 has a phosphor plate for converting X-rays into light, and a plurality of solid-state detection elements aligned in a matrix on the rear surface of the phosphor plate. The solid-state detection elements convert the converted light into electrical signals. The planar type X-ray detector 31 suspends from the other end of a C-shaped arm 25 through a suspension mechanism 33. The planar type X-ray detector 31 is lighter than the total weight of the image intensifier 22, optical system 23, and TV camera 3, and is compact. Hence, in addition to a mechanism for sliding (direction E) the planar type X-ray detector 31, the suspension mechanism 33 has a mechanism for axially rotating (direction I) the planar type X-ray detector 31 and a mechanism for tilting (direction J) the planar type X-ray detector 31.

In the case of FIG. 2, the radiography position is determined by the axial rotation (direction I) of the planar type X-ray detector 31 and the tilt (direction J) of the planar type X-ray detector 31, as well as the vertical motion (direction A) of an arm holder 24, the main rotation (direction B) of the arm holder, the swing (direction C) of the arm holder 24, the sliding rotation motion (direction D) of the C-shaped arm 25, the slide motion (direction E) of the planar type X-ray detector 31, the vertical motion (direction F) of a bed top 28, the longitudinal motion (direction G) of the bed top 28, and the lateral motion (direction H) of the bed top 28.

Figure 3:
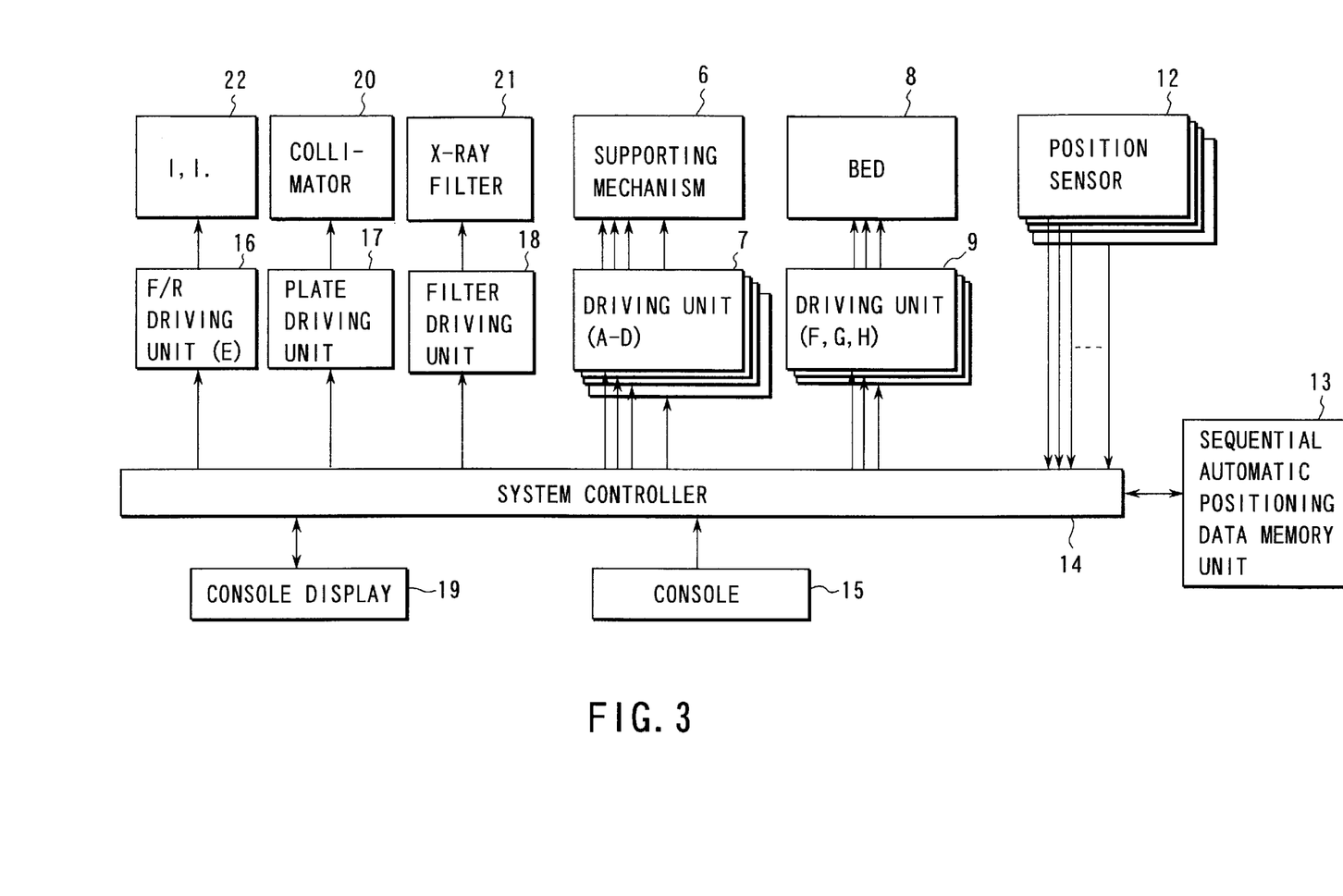
FIG. 3 is a block diagram of that portion of the apparatus of this embodiment which concerns sequential automatic positioning.

FIG. 3 shows the configuration of that portion of this embodiment which concerns sequential automatic positioning. A plurality of radiography positions, together with their order relation, are stored in a memory unit 13 as sequential automatic positioning data. The sequential automatic positioning data includes, in addition to the radiography positions and their order relation, the aperture of the collimator 20 and the position of the X-ray filter 21. The memory unit 13 stores a plurality of items of sequential automatic positioning data. The radiography position and/or its order relation change between data items.

The memory unit 13 is connected to a system controller 14. The system controller 14 is a control center which supervises the sequential automatic positioning function with which the radiography position is sequentially, automatically changed during radiography in accordance with the sequential automatic positioning data. The sequential automatic positioning function and other functions will be described later. To perform the sequential automatic positioning function, the system controller 14 is connected to a plurality of driving units 7, driving unit 16, and plurality of driving units 9. The driving units 7 respectively correspond to the movable portions (the vertical motion (direction A) of the arm holder 24, the main rotation (direction B) of the arm holder 24, the swing (direction C) of the arm holder 24, and the sliding rotation movement (direction D) of the C-shaped arm 25) of the supporting mechanism 6. The driving unit 16 drives the image intensifier 22 to slide (direction E). The driving units 9 respectively correspond to the movable portions (the vertical motion (direction F), the longitudinal motion (direction G), and the lateral motion (direction H)) of the bed top 28. The system controller 14 is also connected to a plate driving unit 17 for adjusting the aperture of the collimator 20, and to a filter driving unit 18 for moving the X-ray filter 21. The system controller 14 is also connected to a plurality of position sensors 12 for detecting the positions of all the movable positions, including the vertical motion of the arm holder 24.

The operation of this embodiment will be described.
(Registration of Sequential Automatic Positioning Data)

Figure 4:
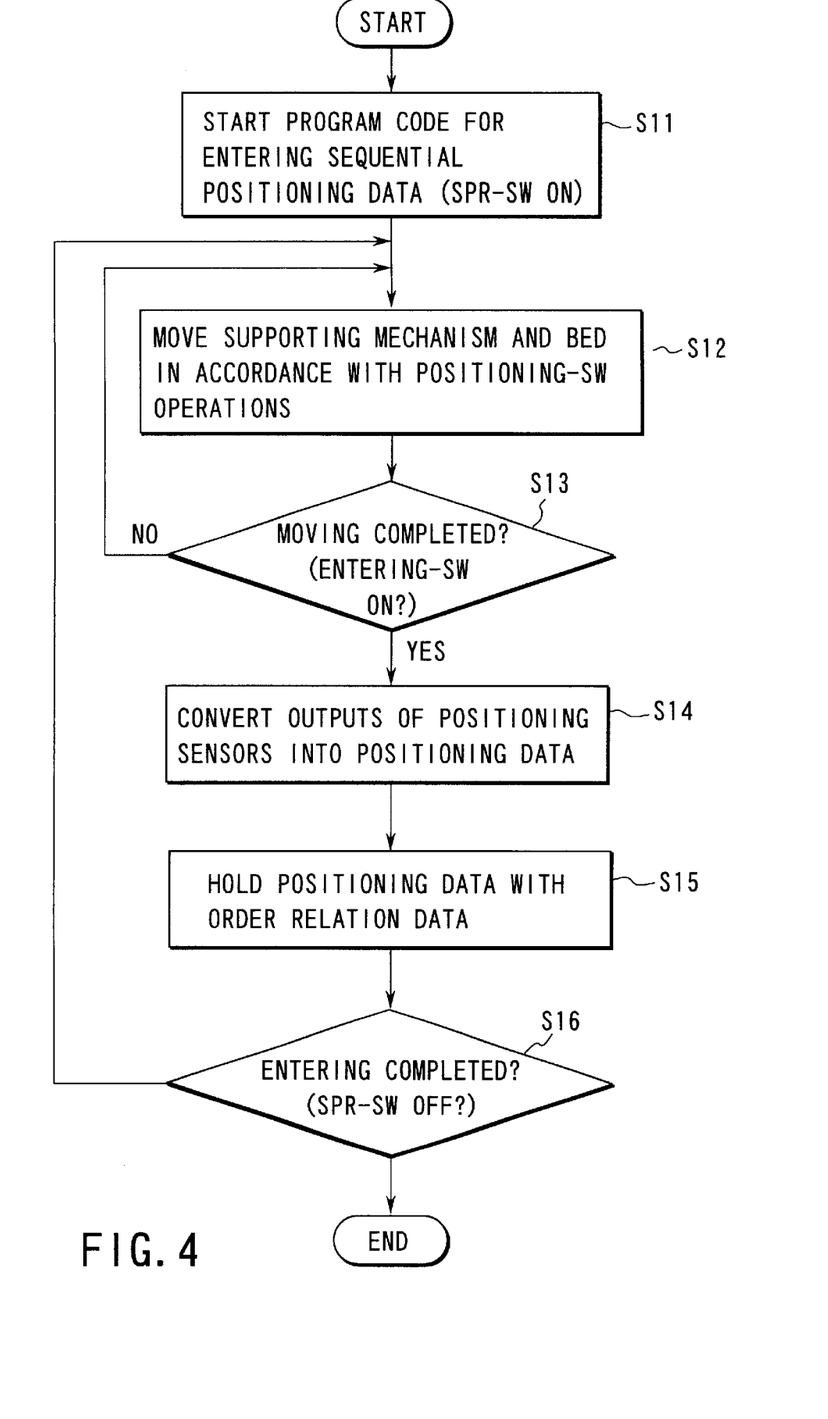
FIG. 4 is a flow chart showing the registration sequence for sequential automatic positioning data in this embodiment.

FIG. 4 shows the registration sequence for the sequential automatic positioning data in this embodiment. When the operator turns on a sequential automatic positioning registration switch (SPR-SW) on a console 15, a sequential automatic positioning registration program is started in the system controller 14 (Step S11). The operator operates a manual lever on the console 15 to set a radiography position (Step S12).

When the radiography position is determined, the operator presses a memory switch on the console 15 (Step S13). The system controller 14 converts outputs from the position sensors 12 into positioning data (Step S14). The positioning data is held together with their registration order, in this case, the order relation of 1.

The routine of Steps S11 to S15 is repeated until the operator turns off the sequential automatic positioning registration switch (SPR-SW) on the console 15 in Step S16. Hence, a plurality of radiography positions (positioning data) are held, together with their order relations, as sequential automatic positioning data.

Figure 5:
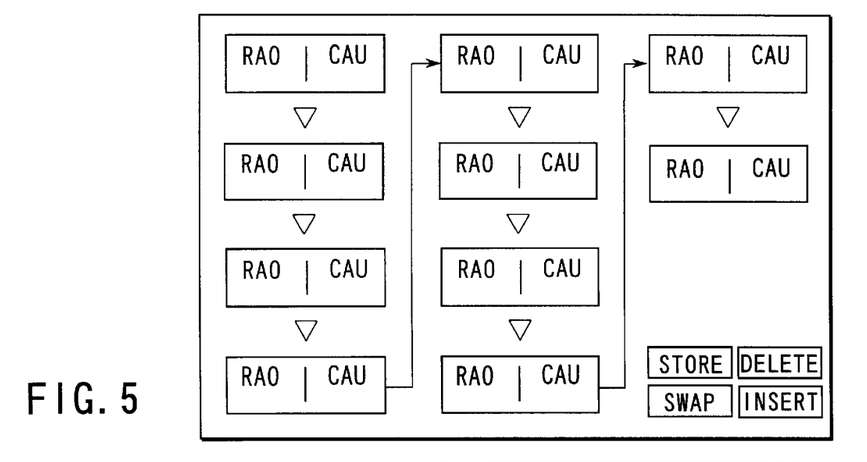
FIG. 5 is a view showing a registration/edit window for the sequential automatic positioning data in this embodiment.

FIG. 5 shows a confirmation/edit window for the sequential automatic positioning data. The sequential automatic positioning data is graphically displayed on a console display 19. Graphic boxes simply indicating the plurality of radiography positions included in the sequential automatic positioning data are displayed in accordance with their order. Each graphic box shows the angle (RAO/LAO) of the C-shaped arm 25 in the direction B and the angle (CRA/CAU) of the C-shaped arm 25 in the direction D as the typical position elements in the corresponding radiography position. The radiography position corresponding to the graphic box specified by a user instruction input through the console 15 is displayed in detail upon switching the graphic box window. On this window, the operator can edit the sequential automatic positioning data by using the functions of deleting the graphic box, swapping the order of the graphic boxes, and inserting a new graphic box, through operation from the console 15. The finally determined sequential automatic positioning data is stored in the memory unit 13.

(Selection of Sequential Automatic Positioning Data)

Figure 6:
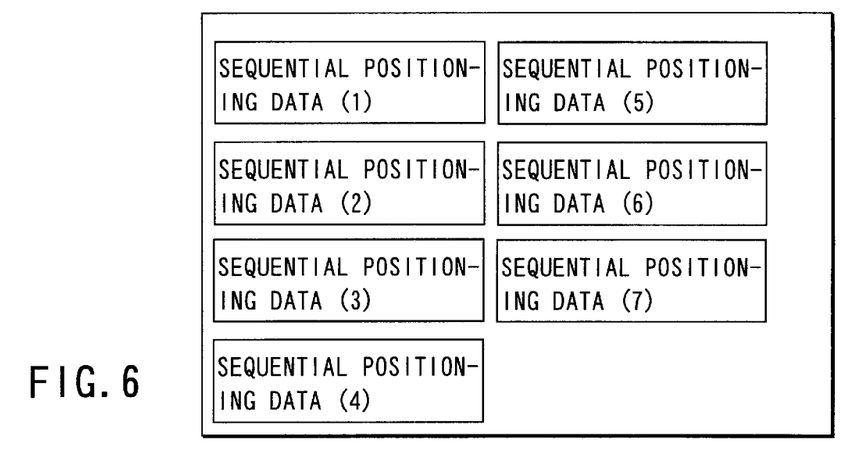
FIG. 6 is a view showing a selection window for the sequential automatic positioning data in this embodiment.
Figure 7:
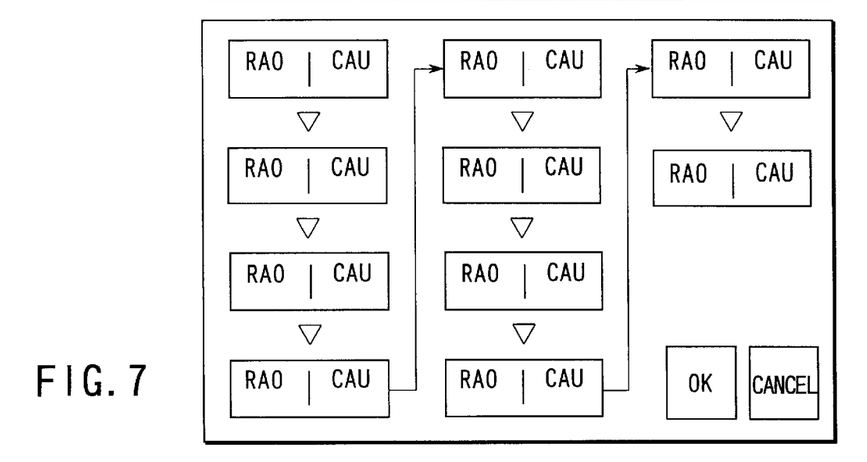
FIG. 7 is a view showing a confirmation window for selected sequential automatic positioning data in this embodiment.

Prior to radiography, desired sequential automatic positioning data is selected from those registered in the memory unit 13. FIG. 6 shows the main window showing the desired sequential automatic positioning data. In FIG. 6, seven different sequential automatic positioning data are graphically displayed as graphic boxes showing additional information such as the radiography position and radiography method. When the operator specifies an arbitrary box from these boxes, sequential automatic positioning data corresponding to the specified graphic box is graphically displayed, as shown in FIG. 7, such that the graphic boxes simply showing the plurality of radiography positions included in this data are arranged in accordance with their order. When the operator further specifies an arbitrary graphic box among these boxes, the radiography position corresponding to the specified box is displayed in detail upon switching the graphic box window. The operator confirms the sequential automatic positioning data in this manner, and instructs "OK (confirmed)" or "cancel (select again)".

(Radiography Operation Using Selected Sequential Automatic Positioning Data)

Figure 8:
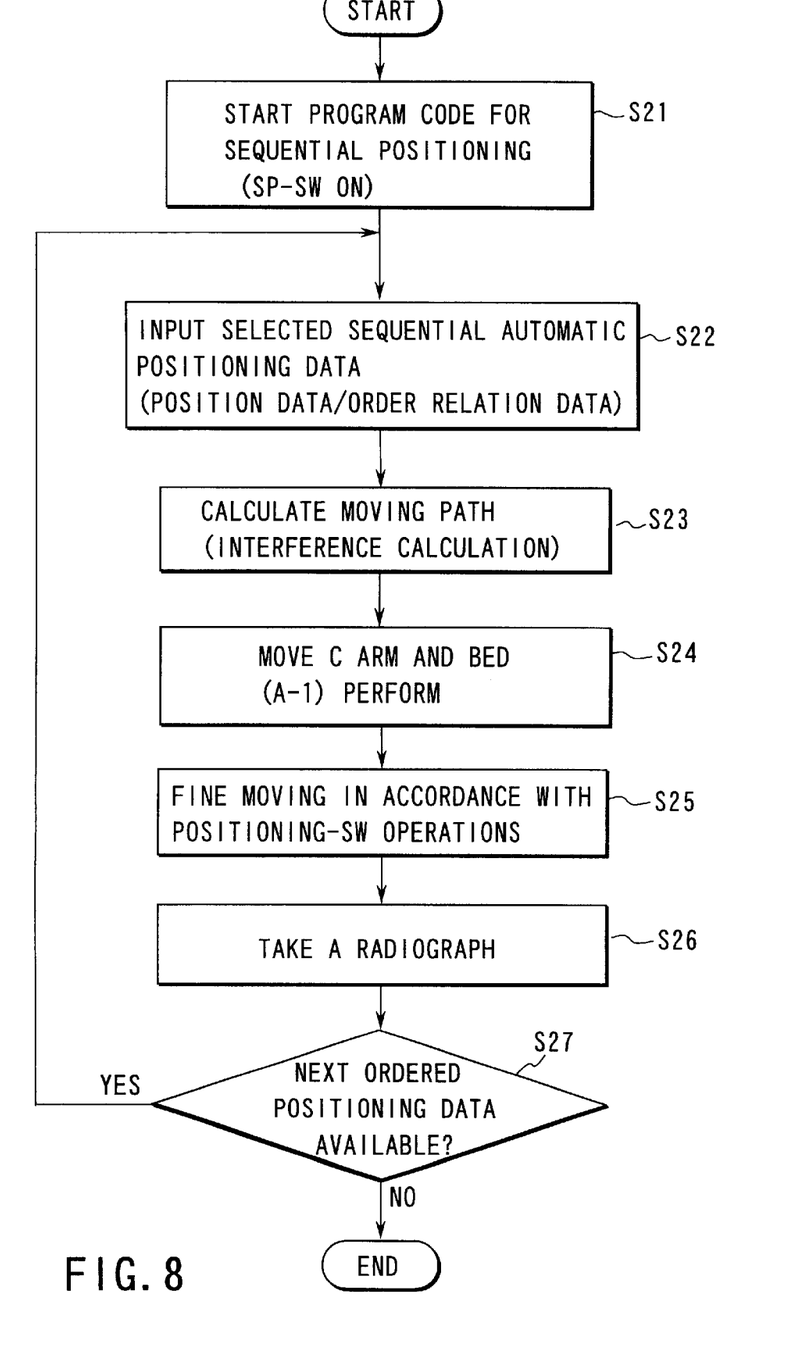
FIG. 8 is a flow chart showing the radiography procedure using the sequential automatic positioning data in this embodiment.

FIG. 8 shows the radiography procedure performed by using the sequential automatic positioning data of this embodiment. When the operator turns on the sequential automatic positioning switch (SP-SW) on the console 15, the radiography program is started in the system controller 14 (Step S21). The selected sequential automatic positioning data is read out from the memory unit 13 by the system controller 14 (Step S22).

Figure 9:
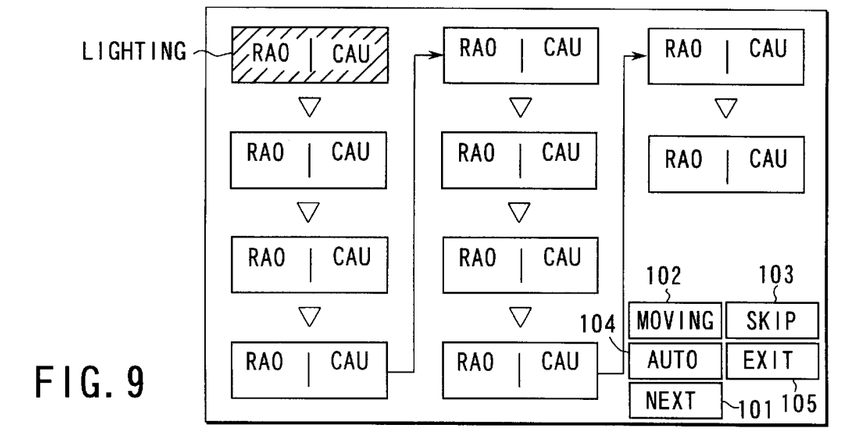
FIG. 9 is a view showing a display window during taking a radiograph in this embodiment.

During this radiography, the sequential automatic positioning data is graphically displayed, as shown in FIG. 9.

The system controller 14 calculates a path along which the C-shaped arm 25 moves from the present position to the first radiography position, i.e., the moving distances of the plurality of movable portions (A–E) and rotation angles of the supporting mechanism 6 and their orders (Step S23). This moving path calculation includes interference calculation for avoiding interference with the bed 8, the bed top 28, the subject, and any other surrounding atmosphere.

When this path calculation is completed, the system controller 14 controls the plurality of driving units 7, 9, 16, 17, and 18 in accordance with their moving paths so as to move the C-shaped arm 25, bed top 28, image intensifier 22, collimator 20, and filter 21 (Step S24). When necessary, the operator appropriately operates the positioning switch on the console 15 to finely move the positions of the C-shaped arm 25, the bed top 28, and the like (Step S25). An X-ray radiograph is taken at this radiography position (Step S26).

During radiography, the graphic box corresponding to this radiography position is displayed differently from other boxes. For example, as shown in FIG. 9, the graphic box corresponding to the radiography position during radiography is lit brighter than other boxes.

When the radiograph is taken at this position, the operator clicks a NEXT button 101 (Step S27). Then, steps S22 to S26 are performed again, and the radiography position is changed to a next one in the sequential automatic positioning data.

Figure 10:
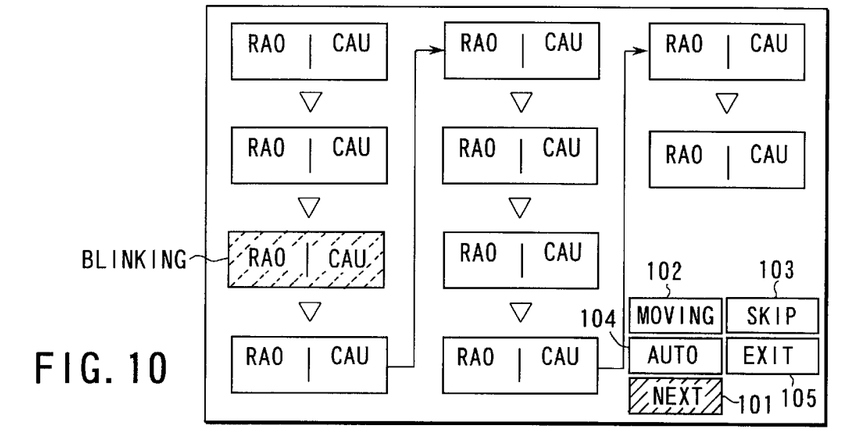
FIG. 10 is a view showing a display window during position change performed in response to NEXT button operation.
Figure 11:
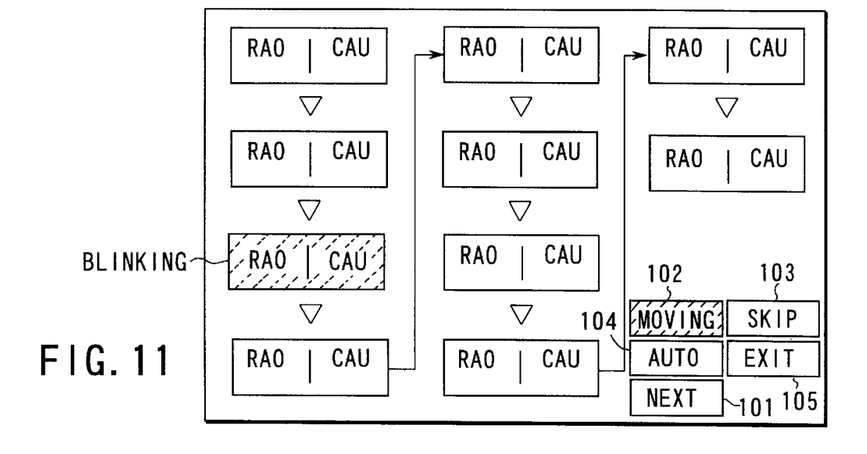
FIG. 11 is a view showing a display window after position change performed in response to MOVING button operation.

While the radiography position is being changed, The corresponding graphic box is displayed differently from other boxes, as shown in FIG. 10. For example, a graphic box corresponding to a radiography position which is being changed flashes. The radiography position can be changed also by operating a MOVING button 102 in place of the NEXT button 101. The operator continuously clicks the MOVING button 102. During this continuous clicking, the C-shaped arm 25 and the like move. When continuous clicking of the MOVING button 102 is discontinued, the C-shaped arm 25 and the like are stopped. Hence, collision of the C-shaped arm 25 and the like against the subject and the like can be prevented by a simple operation of discontinuing clicking the MOVING button 102.

When the operator clicks a SKIP button 103, the system controller 14 skips the next radiography position and sets the radiography system for the radiography position following the skipped one. When the operator clicks an AUTO button 104, the system controller 14 automatically changes the radiography system for the next radiography position in response to the end of radiography in the subsequent radiography position.

In this manner, the plurality of radiography positions are stored, together with their order relation, as the sequential automatic positioning data. In taking a radiograph, the radiography position is sequentially changed in accordance with the sequential automatic positioning data. As a result, the operability concerning a change in the radiography position is improved more than in the conventional case wherein a preset button is repeatedly selected.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image radiography apparatus comprising:
   a radiography system configured to take a medical image of a subject;
   a supporting mechanism configured to support said radiography system in various radiography positions;
   a memory unit configured to store a plurality of radiography positions, together with an order relation thereof, as sequential automatic positioning data, in accordance with operator instructions entered when medical images are being taken; and
   a controller configured to control said supporting mechanism on the basis of the stored sequential automatic positioning data in order to reproduce a plurality of radiography positions, together with an order relation thereof, wherein the radiography positions are sequentially switched with an instructor's position change instruction as a trigger.

2. An apparatus according to claim 1, wherein said supporting mechanism has an arcuate arm for mounting said radiography system thereon, and a mechanism for supporting said arcuate arm to be rotatable at least about three axes, the radiography positions including rotation angles of the three axes.

3. An apparatus according to claim 1, further comprising a bed having a bed top movable in longitudinal and lateral directions, the radiography positions including longitudinal and lateral positions of said bed top.

4. An apparatus according to claim 1, wherein said radiograph system has an X-ray tube, an image intensifier movable in a near/away direction, and a TV camera, the radiography positions including a near/away position of said image intensifier.

5. An apparatus according to claim 1, wherein said radiography system has an X-ray tube and a planar type X-ray detector rotatable about a vertical axis, the radiography positions including a rotation angle of said planar type X-ray detector.

6. An apparatus according to claim 1, wherein said radiography system has an X-ray tube, a collimator arranged between said X-ray tube and the subject, and an X-ray detector, the radiography positions including an aperture of said collimator.

7. An apparatus according to claim 1, wherein said radiography system has an X-ray tube, an X-filter arranged between said X-ray tube and the subject, and an X-ray detector, the radiography positions including a position of said X-ray filter.

8. An apparatus according to claim 1, further comprising a display unit configured to graphically display the sequential automatic positioning data, said display unit displaying graphic boxes, simply showing a plurality of radiography positions included in the sequential automatic positioning data, which are arranged in accordance with an order thereof.

9. An apparatus according to claim 8, wherein said display unit has a function of displaying in detail a radiography position corresponding to a graphic box specified in response to a user instruction.

10. An apparatus according to claim 8, wherein the graphic boxes show typical position elements of the radiography positions corresponding thereto.

11. An apparatus according to claim 8, wherein while the radiography position is being changed, one of the graphic boxes corresponding thereto is displayed differently from other ones.

12. An apparatus according to claim 8, wherein while a radiograph is being taken at an arbitrary radiography position, a graphic box corresponding thereto is displayed differently from other ones.

13. An apparatus according to claim 1, wherein said controller has a function of skipping an arbitrary one of the plurality of radiography positions included in the sequential automatic positioning data in response to a user instruction.

14. An apparatus according to claim 1, further comprising an edit unit configured to have
  a function of graphically displaying the sequential automatic positioning data, the sequential automatic positioning data including a plurality of radiography positions simply indicated by graphic boxes that are arranged in accordance with an order thereof, and
  an edit function of swapping the displayed graphic boxes in response to a user instruction, deleting an arbitrary one in the displayed graphic boxes, and inserting a graphic boxes between arbitrary ones in the displayed graphic boxes.

15. An apparatus according to claim 1, wherein said controller automatically changes a radiography position to a next one in response to an end of radiography in a corresponding radiography position.

16. An apparatus according to claim 1, wherein said controller changes a radiography position to a next one in response to a user instruction.

17. A medical image radiography apparatus comprising:
  means for taking a medical image of a subject;
  means for supporting said image taking means in various radiography positions;
  means for storing a plurality of radiography positions, together with an order relation thereof, as sequential automatic positioning data, in accordance with operator instructions entered when medical images are being taken; and
  means for controlling said supporting means on the basis of the stored sequential automatic positioning data in order to reproduce a plurality of radiography positions, together with an order relation thereof, wherein the radiography positions are sequentially switched with an operator's position change instruction as a trigger.

* * * * *